United States Patent

Moser et al.

Patent Number: 5,223,018
Date of Patent: Jun. 29, 1993

[54] 1-PHENYL-PIPERDINE-2,6-DIONES WITH HERBICIDAL ACTIVITY

[75] Inventors: Hans Moser, Magden, Switzerland; Georg Pissiotas, Lörrach, Fed. Rep. of Germany; Hans-Georg Brunner, Lausen, Switzerland

[73] Assignee: Ciba-Geigy Corporation, Ardsley, N.Y.

[21] Appl. No.: 857,890

[22] Filed: Mar. 26, 1992

Related U.S. Application Data

[63] Continuation-in-part of Ser. No. 819,710, Jan. 13, 1992, abandoned, which is a continuation-in-part of Ser. No. 645,378, Jan. 18, 1991, abandoned, which is a continuation-in-part of Ser. No. 501,650, Mar. 29, 1990, abandoned.

[30] Foreign Application Priority Data

Apr. 4, 1989 [CH] Switzerland ............ 1237/89
Oct. 26, 1989 [CH] Switzerland ............ 3869/89

[51] Int. Cl.$^5$ ............ A01N 43/40; C07D 211/40; C07D 401/10; C07D 413/10
[52] U.S. Cl. ............ 504/221; 504/248; 504/193; 504/225; 504/235; 504/249; 544/60; 544/130; 544/360; 546/188; 546/197; 546/207; 546/208; 546/219; 546/220
[58] Field of Search ............ 546/207, 208, 219, 220, 546/213, 214, 188, 197, 193; 544/60, 130, 365, 360; 514/63, 272.8, 231.5, 255, 316, 326, 327; 71/94, 92

[56] References Cited

U.S. PATENT DOCUMENTS

| | | | |
|---|---|---|---|
| 3,637,825 | 1/1972 | Ackerman | 546/219 |
| 3,745,170 | 7/1973 | Fujinami | 546/219 |
| 4,031,088 | 6/1977 | Ackermann | 260/247 |
| 4,208,202 | 6/1980 | Tobler | 71/88 |

FOREIGN PATENT DOCUMENTS

| | | |
|---|---|---|
| 0415642 | 3/1991 | European Pat. Off. |
| 993156 | 5/1965 | United Kingdom ............ 546/70 |
| 8810254 | of 0000 | World Int. Prop. O. |

OTHER PUBLICATIONS

Pfeifer et al "Biotransformation . . . " CA 77(17) 110113m (1972).
Chem Abstract, 106,84339k (T. Komeatani), Tetrahedron Letters, 1986, 919–22.

*Primary Examiner*—C. Warren Ivy
*Assistant Examiner*—Celia Chang
*Attorney, Agent, or Firm*—Kevin T. Mansfield; Edward McC. Roberts

[57] ABSTRACT

The invention relates to new 1-phenyl-piperidine-2,6-diones of the formula I

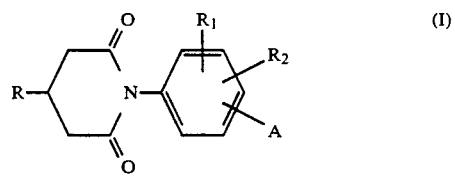

wherein
R is $C_3$–$C_7$-cycloalkyl,
$R_1$ is hydrogen or halogen;
$R_2$ is hydrogen, cyano, nitro or halogen; and
A is hydrogen, cyano, nitro or is an ether or carboxylic acid radical as defined in the description. The salts, complexes as well as the stereoisomeric forms of these compounds, their preparations, use and agrochemical compositions which contains them form also part of this invention.

13 Claims, No Drawings

1-PHENYL-PIPERDINE-2,6-DIONES WITH HERBICIDAL ACTIVITY

This is a continuation-in-part of application Ser. No. 07/819,710, filed Jan. 13, 1992 which is a continuation-in-part of application Ser. No. 07/645,378, filed Jan. 18, 1991 which is a continuation-in-part of application Ser. No. 07/501,650 filed Mar. 29, 1990, all abandoned.

The invention relates to new 1-phenyl-piperidine-2,6-diones of the formula I

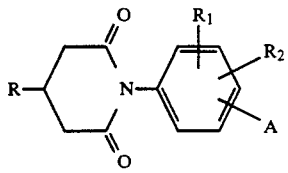

wherein
R is $C_3$–$C_7$-cycloalkyl;
$R_1$ is hydrogen; or halogen;
$R_2$ is hydrogen; cyano; nitro; or halogen;
A is hydrogen; cyano; nitro; $COR_3$; $XR_4$;

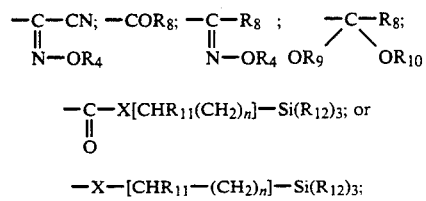

$R_3$ is halogen; $X'$–$R_5$; amino; $C_1$–$C_4$-alkylamino; di-$C_1$–$C_4$-alkylamino; $C_2$–$C_4$-halogen-alkylamino; $C_1$–$C_4$-hydroxyalkylamino; di-$C_1$–$C_4$-hydroxyalkylamino; $C_3$–$C_4$-alkenylamino; diallylamino; N-pyrrolidino; N-piperidino; N-morpholino; N-thiomorpholino; or N-piperazino;
$R_4$ is hydrogen; $C_1$–$C_{10}$-alkyl; $C_1$–$C_4$-alkoxy-$C_1$–$C_4$-alkyl; $C_1$–$C_4$-alkylthio-$C_1$–$C_4$-alkyl; di-$C_1$–$C_4$-alkylamino-$C_1$–$C_4$-alkyl; halo-$C_1$–$C_8$-alkyl; $C_3$–$C_8$-alkenyl; halo-$C_2$–$C_8$-alkenyl; $C_3$–$C_8$-alkynyl; $C_3$–$C_7$-cycloalkyl; halo-$C_3$–$C_7$-cycloalkyl; $C_1$–$C_8$-alkylcarbonyl; allylcarbonyl; $C_3$–$C_7$-cycloalkylcarbonyl; benzoyl unsubstituted or substituted at the phenyl ring identically or differently up to three times by halogen, $C_1$–$C_4$-alkyl, halo-$C_1$–$C_4$-alkyl, halo-$C_1$–$C_4$-alkoxy, or $C_1$–$C_4$-alkoxy; furanoyl; thiophenoyl; $C_1$–$C_4$-alkyl that is substituted by phenyl, halophenyl, $C_1$–$C_4$-alkylphenyl, $C_1$–$C_4$-alkoxyphenyl, halo-$C_1$–$C_4$-alkylphenyl, halo-$C_1$–$C_4$-alkoxyphenyl, $C_1$–$C_6$-alkoxycarbonyl, $C_1$–$C_4$-alkoxy-$C_1$–$C_8$-alkoxycarbo-nyl, $C_3$–$C_8$-alkenyloxycarbonyl, $C_3$–$C_8$-alkynyloxycarbonyl, $C_1$–$C_6$-alkylthiocarbonyl, $C_3$–$C_8$-alkenylthiocarbonyl, $C_3$–$C_8$-alkynylthiocarbonyl, carbamoyl, mono-$C_1$–$C_4$-alkylaminocarbonyl, di-$C_1$–$C_4$-alkylaminocarbonyl, phenylaminocarbonyl, wherein the phenyl ring is unsubstituted or identically or differently substituted up to three times by halogen, $C_1$–$C_4$-alkyl, halogen-$C_1$–$C_4$-alkyl, halogen-$C_1$–$C_4$-alkoxy, or $C_1$–$C_4$-alkoxy, or the phenyl is monosubstituted by cyano or nitro; dioxan-2-yl which is unsubstituted or substituted by one or two $C_1$–$C_4$-alkyl radicals; or $C_1$–$C_4$-alkyl substituted by cyano, nitro, carboxyl, $C_1$–$C_8$-alkylthio-$C_2$–$C_8$-alkoxycarbonyl or $C_1$–$C_8$-alkoxy-$C_2$–$C_8$-alkoxycarbonyl;
X is oxygen; or sulfur;
$X'$ is oxygen; or sulfur;
$R_5$ is hydrogen; $C_1$–$C_{10}$-alkyl; $C_1$–$C_4$-alkoxy-$C_1$–$C_4$-alkyl; halo-$C_1$–$C_8$-alkyl; $C_1$–$C_{10}$-alkylthio-$C_1$–$C_4$-alkyl; di-$C_1$–$C_4$-alkylamino-$C_1$–$C_4$-alkyl; cyano-$C_1$–$C_{10}$-alkyl; $C_3$–$C_8$-alkenyl; halogen-$C_3$–$C_8$alkenyl; $C_3$–$C_8$-alkynyl; $C_3$–$C_7$-cycloalkyl; $C_3$–$C_7$-cycloalkyl-$C_1$–$C_4$-alkyl; halo-$C_3$–$C_7$-cycloalkyl; benzyl which is unsubstituted or substituted in the phenyl ring identically or differently up to three times by halogen, $C_1$–$C_4$-alkyl, halo-$C_1$–$C_4$-alkyl, halo-$C_1$–$C_4$-alkoxy or $C_1$–$C_4$-alkoxy; an alkaline-, alkaline-earth- or an ammonium-ion; or the group —[$CHR_6(CH_2)_n$]—$COOR_7$;
$R_6$ is hydrogen; or $C_1$–$C_4$-alkyl;
$R_7$ is hydrogen; $C_1$–$C_6$-alkyl; $C_3$–$C_8$-alkenyl; $C_3$–$C_8$-alkynyl; $C_1$–$C_8$-alkoxy-$C_2$–$C_8$-alkyl; $C_1$–$C_8$-alkylthio-$C_2$–$C_8$-alkyl; or $C_3$–$C_7$-cycloalkyl;
$R_8$ hydrogen; $C_1$–$C_4$-alkyl; halogen-$C_1$–$C_4$-alkyl; or $C_1$–$C_4$-alkoxy-$C_1$–$C_4$-alkyl;
$R_9$ and $R_{10}$ independently of each other are $C_1$–$C_4$-alkyl; $C_2$–$C_4$-haloalkyl; or $C_2$–$C_8$-alkoxyalkyl; or
$R_9$ and $R_{10}$ together form an ethylene- or propylene-bridge or a 1,2-cyclohexanyl-ring, which radicals can be unsubstituted or substituted by one or two substituents selected from among halogen, $C_1$–$C_4$-alkyl, $C_1$–$C_4$-haloalkyl or $C_1$–$C_4$-hydroxyalkyl;
$R_{11}$ is hydrogen; $C_1$–$C_5$-alkyl; or $C_3$–$C_7$-alkenyl;
$R_{12}$ is independently of each other hydrogen; or $C_1$–$C_8$-alkyl;
n is zero;, 1; 2; 3; or 4;
and to the salts, or complexes which the compounds of the formula I can form with acids, bases and complex-formers as well as to the stereoisomeric forms of the compounds of the formula I.

The definitions used in this description enclose the given generic notion as well as the separate meanings, which can be obtained by combining single sub-species, such as the substituents listed below. The following enumeration is not limiting the invention.

Alkyl represents e.g. methyl, ethyl, n-propyl, isopropyl, n-butyl, sec.-butyl, isobutyl, tert.-butyl as well as the isomers of pentyl and hexyl. The $C_1$–$C_4$-alkyl radicals are preferred.

Halogen includes fluorine, chlorine, bromine, and iodine, preferably chlorine and bromine.

Alkoxy is e.g. methoxy, ethoxy, propyloxy, isopropyloxy, n-butyloxy, isobutyloxy, sec.-butyloxy and tert.-butyloxy, preferably methoxy or ethoxy.

Haloalkyl is e.g. fluoromethyl, difluoromethyl, trifluoromethyl, chloromethyl, dichloromethyl, trichloromethyl, 2,2,2-trifluoroethyl, 2-fluoroethyl, 2-chloroethyl and 2,2,2-trichloroethyl, preferably chloromethyl, 2-chloromethyl, trifluoromethyl, pentafluoroethyl and 2,2,2-trifluoro-1-methylethyl.

Haloalkoxy is e.g. fluoromethoxy, difluoromethoxy, trifluoromethoxy, 2,2,2-trifluoroethoxy, 1,1,2,2-tetrafluoroethoxy, 2-fluoroethoxy, 2-chloroethoxy and 2,2,2-trichloroethoxy, preferably difluoromethoxy, 2-chloroethoxy and trifluoromethoxy.

Alkoxycarbonyl is e.g. methoxycarbonyl, ethoxycarbonyl, n-propyloxycarbonyl, iso-propyloxycarbonyl and n-butyloxycarbonyl, preferably methoxycarbonyl and ethoxycarbonyl.

Alkoxyalkyl is e.g. methoxymethyl, ethoxymethyl, n- or iso-propyloxymethyl, methoxyethyl, ethoxyethyl, n- or iso-propyloxyethyl, methoxy-n-propyl, ethoxy-n-propyl or n- or iso-propyloxypropyl.

Alkylthioalkyl is e.g. methylthiomethyl, ethylthiomethyl, methylthioethyl, ethylthioethyl or isopropylthioethyl.

Alkylaminoalkyl is e.g. methylaminoethyl, dimethylaminoethyl, ethylaminoethyl or diethylaminoethyl.

Cyanoalkyl is e.g. cyanomethyl, cyanoethyl or cyanopropyl.

Alkenyl is e.g. allyl, 2-butenyl, 3-butenyl or methallyl, preferably however allyl.

Alkynyl is e.g. propynyl, 2-butyryl or 3-butyryl, preferably however propynyl.

Cycloalkyl is e.g. cyclopropyl, cyclobutyl, cyclopentyl, cyclohexyl or cycloheptyl. Preferred are cyclopentyl and cyclohexyl.

Halogencycloalkyl is e.g. 2,2-dichlorocyclopropyl or pentachlorohexyl.

Cycloalkylcarbonyl is e.g. cyclopentyloxycarbonyl or cyclohexyloxycarbonyl.

Phenyl also as a part of a substituent like phenoxy, phenylthio, phenoxycarbonyl, phenylaminocarbonyl, benzyl or benzoyl, can generally be unsubstituted or substituted by other substituents. The substitution can be in ortho-, meta- and or para-position. Preferred positions for substitution are the ortho- and para-position in respect to the ring-link. Preferred substituents are halogen atoms.

In other substituents, which are composed from different basic elements, these elements have the above given meanings. Also these enumerations have an illustrating character, they do not limit the invention in any case.

Among the compounds of this invention, those are preferred, which correspond to one of the following formulae:

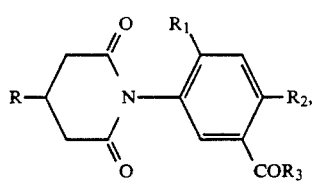
(Ib)

wherein R, $R_1$, $R_2$ and $R_3$ have the meanings given under formula I;

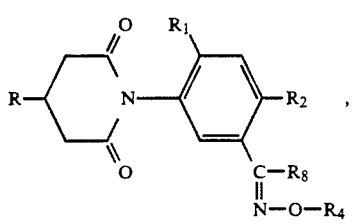
(Ic)

wherein R, $R_1$, $R_2$, $R_4$ and $R_8$ have the meanings given under formula I;

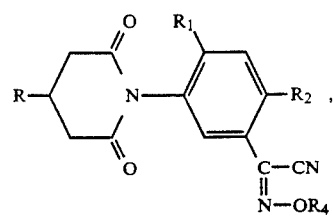
(Id)

wherein R, $R_1$, $R_2$ and $R_4$ have the meanings given under formula I;

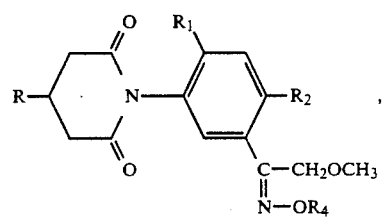
(Ie)

wherein R, $R_1$, $R_2$ and $R_4$ have the meanings given under formula I;

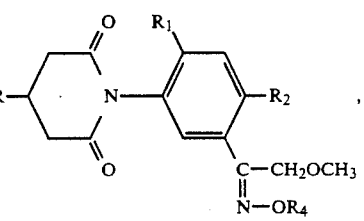
(If)

wherein R, $R_1$, $R_2$, $R_8$, $R_9$ and $R_{10}$ have the meanings given under formula I;

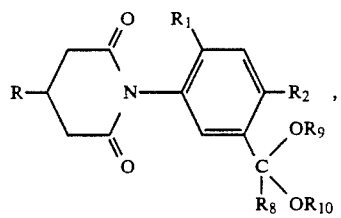
(Ig)

wherein R, $R_1$, $R_2$, and $R_8$ have the meanings given under formula I;

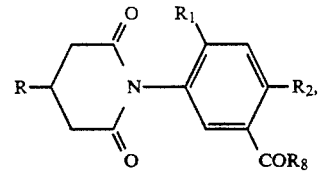
(Ih)

wherein R, $R_1$, $R_2$, $R_4$ and X have the meanings given under formula I;

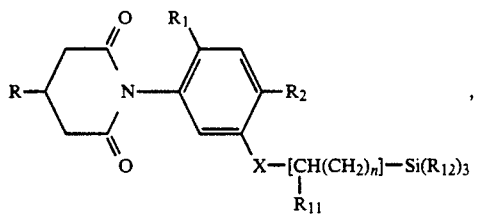

wherein n, R, $R_1$, $R_2$, $R_{11}$, $R_{12}$ and X have the meanings given under formula I;

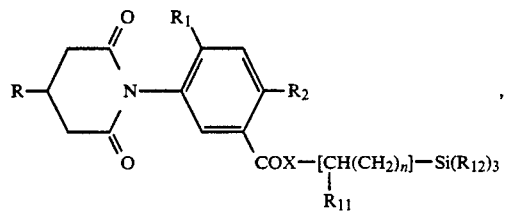

wherein n, R, $R_1$, $R_2$, $R_{11}$, $R_{12}$ and X have the meanings given under formula I;

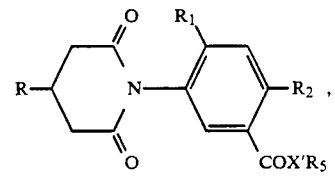

wherein R, $R_1$, $R_2$, $R_5$ and X' have the meanings given in formula I.

Preferred a further compounds of the formula (I), especially those of formulae (Ib), (Ic), (Id), (Ie), (If), (Ig), (Ih), (Ii), (Ij) and (Ik), wherein R is cyclopropyl.

Especially preferred are compounds of the formula (I), especially those of formulae (Ib), (Ic), (Ig), (Ih) and (Ik), wherein R is cyclopropyl;
$R_1$ is fluorine or hydrogen, especially fluorine; and/or
$R_2$ is chlorine; and/or A is —COOH, —COO—C-$_1$-C$_{10}$-alkyl, —O—C$_1$-C$_{10}$-alkyl, propin-3-yl, 3-methylpropin-3-yl or

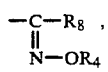

wherein $R_8$ is methyl and $R_4$ is $C_1$-$C_{10}$-alkyl, halo-$C_2$-$C_8$-alkenyl or $C_1$-$C_6$-alkoxycarbonyl-$C_1$-$C_4$-alkyl; especially wherein A is —COOH, —COOCH$_3$, —COOC$_2$H$_5$, —COO(n)C$_3$H$_7$, —COO(n)C$_5$H$_{11}$, —O—CH$_3$, —O—C$_2$H$_5$, —O—(i)C$_3$H$_7$, —O—(n)C$_4$H$_9$, —O—(i)C$_4$H$_9$, —O—(sek)C$_4$H$_9$, propin-3-yl, 3-methylpropin-3-yl or

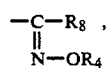

wherein $R_8$ is methyl and $R_4$ is methyl, 1-chloropropen-3-yl or —CH(CH$_3$)—COOCH$_3$.

The invention relates besides to the salts and complexes, which these compounds can form with acids, bases and complex-formers, also to all the possible stereoisomers which can occur in the form of enantiomers, diastereomers, or the mixtures thereof.

The compounds of the formula I are new. They can be produced e.g. by reaction of glutaric acid anhydrides of the formula II with amines of the formula III, whereby the substituents R, $R_1$, $R_2$ and A are as defined under formula I, to glutaric acid anilides of the formula IV and subsequent ring-closure of the monoamide of the formula IV by means of a condensation agent, to form the piperidine-2,6-dione of the formula I

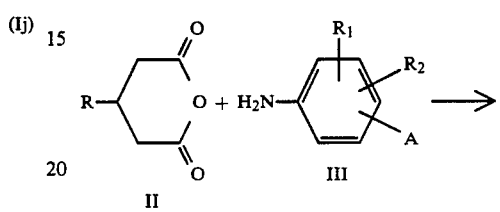

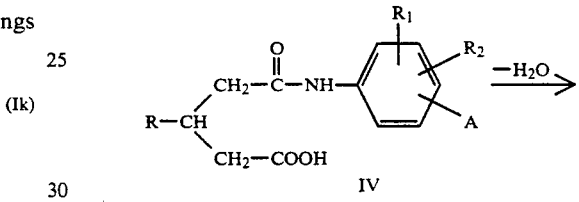

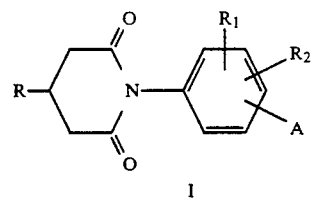

The compounds of formulae II and III are known or can be prepared analogously to known processes. The glutaric acid amides of the formula IV however are new. The novel compounds of the formula IV are precious intermediates for the production of the end-products of formula I of this invention.

The invention therefore also relates to the new glutaric amides of the formula IV, wherein the substituents R, $R_1$, $R_2$ and A are as defined under formula I.

For the synthesis of glutaric acid anhydrides which are substituted in the 3-position, there are described different processes in the literature.

The reaction-sequence shown in scheme 1 is among others very appropriate for the production of the compounds of the formula II. It starts from the very basic, generally available starting materials (aldehyde and cyanoacetic acid ester).

Scheme 1

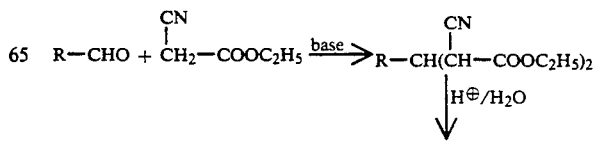

-continued
Scheme 1

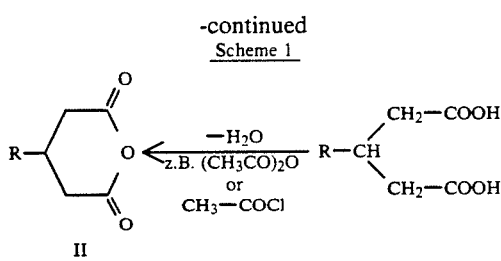

The process according to scheme 1 is described among others in the following literature: J. Chem. Soc. 117 (1920) 1465; J. Chem. Soc. 123 (1923), 3131; J. Chem. Soc. 1952, 4785; Rec. Trav. Chim. Pays-Bas 84 (1965), 1183 and J. Ind. Chem. Soc. 13 (1936), 322.

Another variation for the preparation of the glutaric acid anhydrides of formula II is based on a malonic ester synthesis and is summarized in scheme 2:

Scheme 2

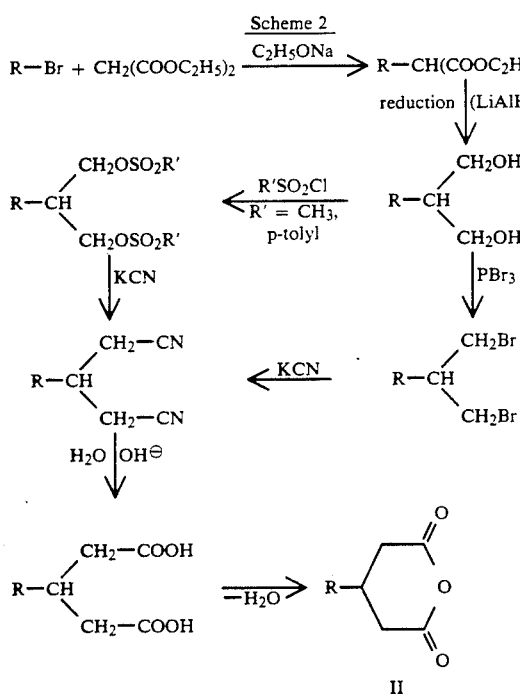

The synthesis outlines in scheme 2 is known among others, from the following literature: Chem. Soc. Perkin Trans. I, 1978, 1636; J. Am. Chem. Soc. 95 (1973), 7437; Org. Prep. Proc. Int. 7, (1975), 283.

Compounds of the formula II, wherein R is cyclopropyl, can e.g. be prepared according to the following scheme 2a:

Scheme 2a

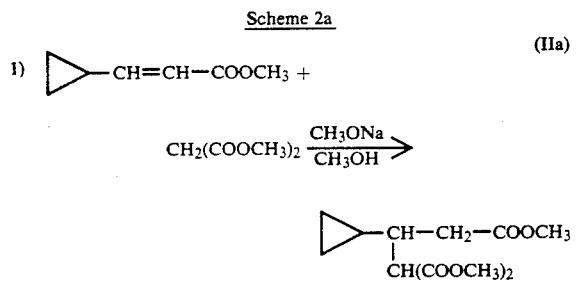

-continued
Scheme 2a

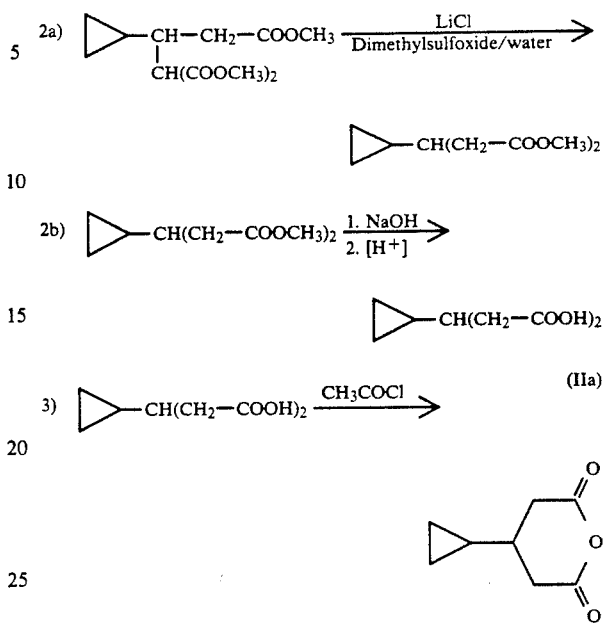

The starting material of the synthesis outlined in scheme 2a is known from the following literature:

J. Org. Chem. 55, 3088 (1990).

In a first step a cyclopropyl-acrylic-acid-ester is reacted with a malonic acid ester to form cyclopropyl-propane-1,1,3-tricarbonic acid ester in presence of methanolic sodium methylate. Cyclopropyl-propane-1,1,3-tricarbonic acid ester is then reacted with LiCl in dimethylsulfoxide and water to form the diester which then forms 3-cyclopropyl glutaric acid. 3-Cyclopropyl-glutaric acid anhydride is formed by reaction of 3-cyclopropyl glutaric acid with acetyl chloride.

The invention relates also to the 3-cyclopropyl glutaric acid anhydride of formula (IIa).

The aniline of the formula III are known from numerous patent publications, among others from the published European Patent applications EP-A 67,714, EP-A 83,055, EP-A 190,755, EP-A 207,894, EP-A 216,243 and EP-A 303 573.

Some of the compounds falling under the formula I are furthermore especially convenient starting materials for the preparation of other derivatives of the formula I.

The invention relates also to the preparation of piperidine-2,6-diones of the formula Ik and Iu,

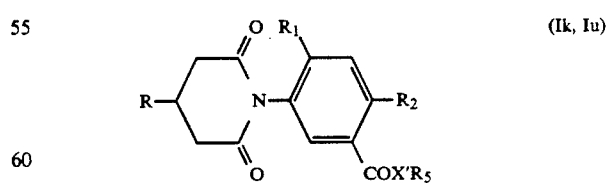

wherein the radicals R, $R_1$, $R_2$, $R_5$ and $X'$ are as defined before which consists in condensing a carbonic acid halide of the formula VIII, wherein the radicals R, $R_1$ and $R_2$ are as defined before and Hal stands for chlorine, bromine or iodine, with an alcohol or thiol of the formula V.

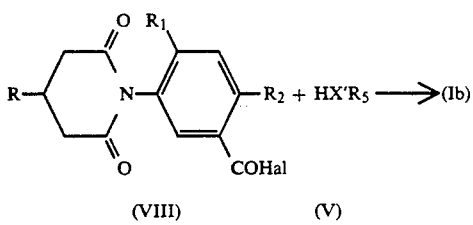

(VIII)    (V)

This reaction is carried out advantageously in the presence of the molecular amount of a base.

The carbonic acid derivatives of the formula Ik and Iu

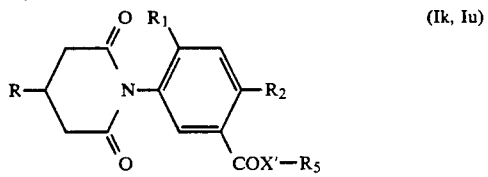

(Ik, Iu)

wherein R, R$_1$, R$_2$, R$_5$ and X' are as defined before, can be prepared by esterifying directly a carbonic acid of the formula VIII with an alcohol or thiol of the formula V in the presence of a water-binding agent

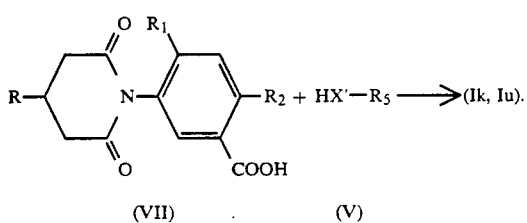

(VII)    (V)

A suitable water-binding agent for the above reaction is e.g. dicyclohexylcarbodiimide.

The ethers of the formulae Ih or It resp.

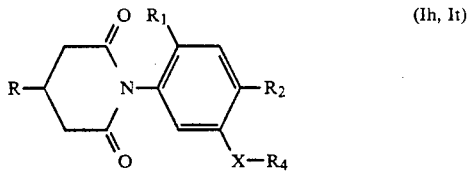

(Ih, It)

wherein the radicals R, R$_1$, R$_2$, R$_4$ and X are as defined before, can be prepared by reacting phenols or thiophenols of the formula IX with compounds of the formula X

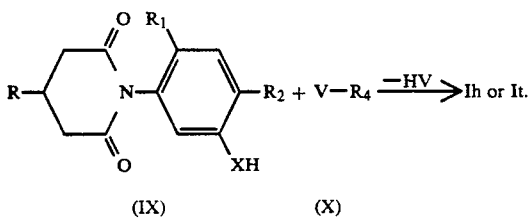

(IX)    (X)

In formula X the symbol V stands for a nucleofuge group, such as halogen, C$_1$–C$_4$-alkylsulfonyl or arylsulfonyl, which can be split off and substituted by another radical under the influence of a base.

The compounds of the formula I are prepared according to this invention, by condensing a glutaric acid anhydride of the formula II

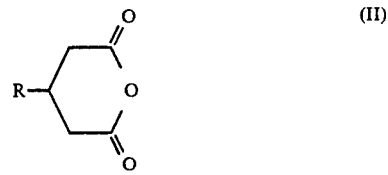

wherein R has the meaning given under formula I, with one amine of the formula III

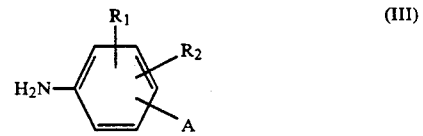

wherein A, R$_1$ and R$_2$ have the meanings given under formula I, to form a glutaric acid-monoanilide of the formula IV,

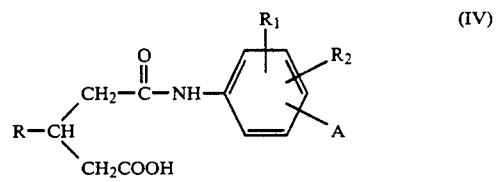

wherein A, R, R$_1$ and R$_2$ have the meanings given under formula I, and subsequently cyclising it by means of a condensing agent, to form a 1-phenylpiperidine-2,6-dione of the formula I

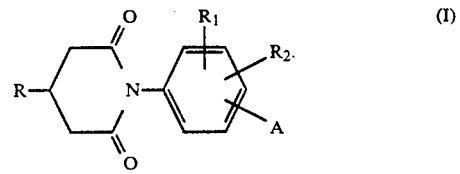

Condensing agents for the above cyclo-condensation are among others acid anhydrides, such as acetic acid anhydride, further acid halides, such as acetyl chloride or thionyl chloride.

The above condensations are advantageously carried out in an inert organic solvent. The reaction temperature is in general between room-temperature and the boiling temperature of the reaction-mixture. The reaction is preferably heated under reflux. The condensation-reaction can be accelerated by adding condensation-catalyst and by eliminating the water that is found during the reaction. Good results are achieved by addition of water-binding agents, such as e.g. sulfuric acid.

Suitable solvents are especially higher boiling carbohydrates, esters and amides, higher boiling ketones and ethers. Examples therefore are benzene, toluene, xylene, dimethylformamide, dimethylacetamide, ethyl acetate, diisopropyl ether, ethyleneglycol methyl ether, tetrahydrofuran, dioxane or 2-butanone, chloroform, tetrachlorocarbon or dichloromethane or methylene chloride.

Although the above outlined synthesis for the compounds of the formula I by condensing an anhydride of the formula II with an aniline of the formula III is practicable in every case, it may be more convenient, for economic or production-technical reasons to transform certain derivatives of the formula I into other derivatives of the formula I. For these transformations, different reactions, known to the skilled in the art, such as e.g. oxydation, reduction, esterification, saponification or amidation can come in question. Examples for such transformations of certain active compounds into other active compounds of the formula I are listed in the following schemes 3 to 5:

-continued
Scheme 3

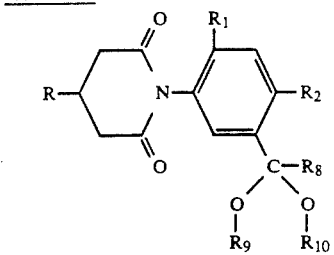

Scheme 4

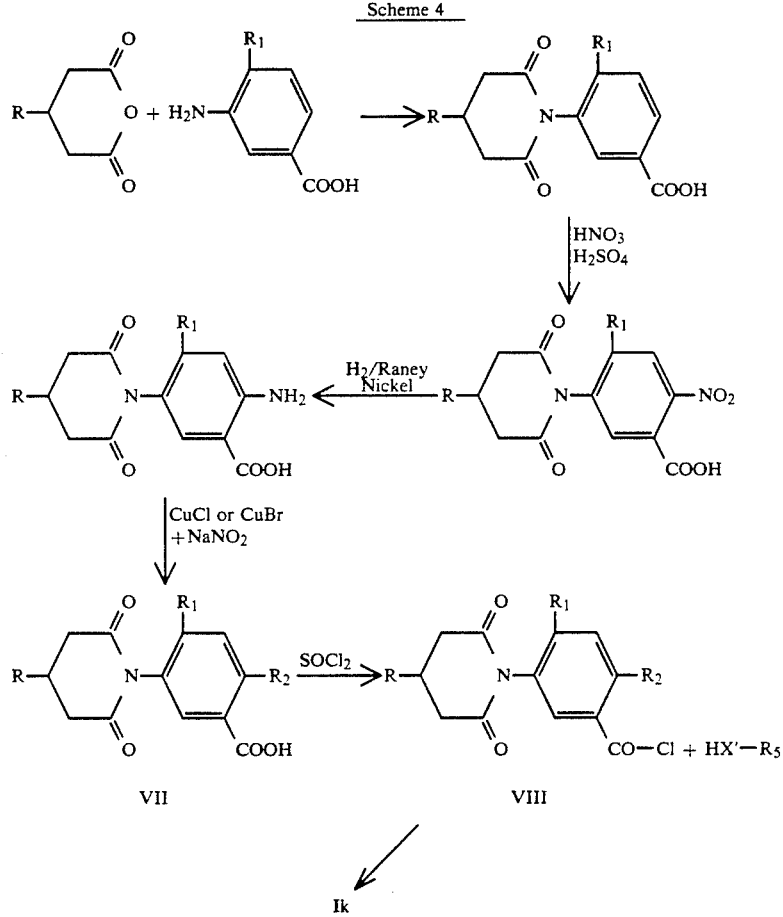

The acid-chlorides of the formula VIII wherein $R_1$ is hydrogen or fluorine, $R_2$ is chlorine or bromine and R is as defined under formula I are important intermediates in the production of imides of the formula I. These chlorides and their production are also a object of this invention.

Scheme 3

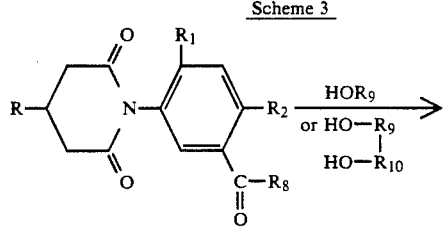

Scheme 5
Hal is chlorine or bromine

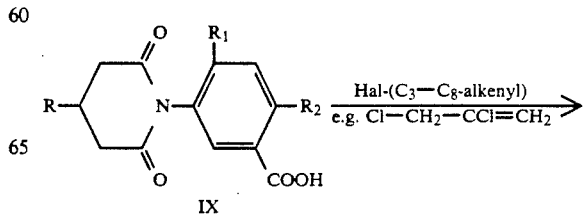

-continued
Scheme 5

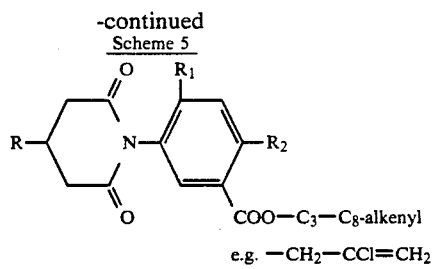

e.g. $-CH_2-CCl=CH_2$

The invention includes all possible stereoisomers which may be present in the form of enantiomers, diastereomers or their mixtures.

The compounds of the formulae Ib, Id and If are thus precious intermediates for the preparation of higher developed compounds of the formula I.

The above mentioned preparations can be carried out in analogy to procedures known from the literature. The preferred reaction conditions of these synthesis e.g. reaction temperatures, molar proportions of the starting materials and components, conduction of the reaction, solvents, special reactants which may be necessary, such as acids, bases, water-binding agents etc. are known to the skilled in the art.

The compounds of the formula I are stable compounds for the handling of which particular precautions are not necessary.

The compounds of formula I are highly active herbicides which, when applied at suitable rates of application, are most suitable for use as selective herbicides for controlling weeds in crops of useful plants. Cultivated plants such as cereal (e.g. rye, barley, oats, wheat), maize, sorghum, rice, cotton, soybeans and sunflowers remain almost undamaged at low rates of application. The growth of cultivated plants is affected to only an insignificant degree when the compounds of formula I are used in higher concentrations. When applied in very high concentrations, the compounds of formula I have total herbicidal properties.

The selective herbicidal activity of the compounds of this invention is observed in preemergence as well as postemergence application. These compounds can therefore be used very successfully for selective weed control when applied pre- and postemergence. The compounds of the formula I are also useful in the so called "no tillage" applications, where the herbicide is used to prepare the soil for seedings without tillage.

The invention also relates to herbicidal and growth regulating compositions which contain a novel compound of formula I, and to methods of controlling weeds pre- and postemergence.

The compounds of formula I are used in unmodified form or, preferably, together with the adjuvants conventionally employed in the art of formulation, and are therefore formulated in known manner to emulsifiable concentrates, directly sprayable or dilutable solutions, dilute emulsions, wettable powders, soluble powders, dusts, granulates, and also encapsulations in e.g. polymer substances. As with the nature of the compositions, the methods of application, such as spraying, atomising, dusting, scattering or pouring, are chosen in accordance with the intended objectives and the prevailing circumstances.

The compounds of the formula I can also be sprayed (coated) onto mineral fertilizers.

The formulations, i.e. the compositions, preparations or mixtures containing the compounds of formula I and, where appropriate, a solid or liquid adjuvant, are prepared in known manner, e.g. by intimately mixing and/or grinding the active components with extenders, e.g. with solvents, solid carriers, and optionally surface-active compounds (surfactants).

Suitable solvents are: aromatic hydrocarbons, preferably the fractions containing 8 to 12 carbon atoms, e.g. xylene mixtures or substituted naphthalenes, phthalates such as dibutyl phthalate or dioctyl phthalate, aliphatic hydrocarbons such as cyclohexane or paraffins, alcohols and glycols and their ethers and esters, such as ethanol, ethylene glycol, ethylene glycol monomethyl or monoethyl ether, ketones such as cyclohexanone, strongly polar solvents such as N-methyl-2-pyrrolidone, dimethyl sulfoxide or dimethylformamide, as well as vegetable oils or epoxidised vegetable oils such as epoxidised coconut oil or soybean oil; or water.

The solid carriers used e.g. for dusts and dispersible powders are normally natural mineral fillers such as calcite, talcum, kaolin, montmorillonite or attapulgite. In order to improve the physical properties it is also possible to add highly dispersed silicic acid or highly dispersed absorbent polymers. Suitable granulated adsorptive carriers are porous types, for example pumice, broken brick, sepiolite or bentonite; and suitable non-sorbent carriers are materials such as calcite or sand. In addition, a great number of pregranulated materials of inorganic or organic nature can be used, e.g. especially dolomite or pulverised plant residues.

Depending on the nature of the compound of formula I to be formulated, suitable surface-active compounds are non-ionic, cationic and/or anionic surfactants having good emulsifying, dispersing and wetting properties. The term "surfactants" will also be understood as comprising mixtures of surfactants.

Suitable anionic surfactants can be both water-soluble soaps and water-soluble synthetic surface-active compounds.

Suitable soaps are e.g. the alkali metal salts, alkaline earth metal salts or unsubstituted or substituted ammonium salts of higher fatty acids ($C_{10}$–$C_{22}$), e.g. the sodium or potassium salts of oleic or stearic acid, or of natural fatty acid mixtures which can be obtained e.g. from coconut oil or tall oil. Mention may also be made of fatty acid methyl taurin salts.

More frequently, however, so-called synthetic surfactants are used, especially fatty sulfonates, fatty sulfates, sulfonated benzimidazole derivatives or alkylarylsulfonates.

The fatty sulfonates or sulfates are usually in the form of alkali metal salts, alkaline earth metal salts or unsubstituted or substituted ammonium salts and contain a $C_8$–$C_{22}$alkyl radical which also includes the alkyl moiety of acyl radicals, e.g. the sodium or calcium salt of lignosulfonic acid, of dodecylsulfate or of a mixture of fatty alcohol sulfates obtained from natural fatty acids. These compounds also comprise the salts of sulfated and sulfonated fatty alcohol/ethylene oxide adducts. The sulfonated benzimidazole derivatives preferably contain 2 sulfonic acid groups and one fatty acid radical containing 8 to 22 carbon atoms. Examples of alkylarylsulfonates are the sodium, calcium or triethanolamine salts of dodecylbenzenesulfonic acid, dibutylnaphthalenesulfonic acid, or of a condensate of naphthalenesulfonic acid and formaldehyde. Also suitable are corresponding phosphates, e.g. salts of the phosphoric acid ester of an adduct of p-nonylphenol with 4 to 14 moles of ethylene oxide, or phospholipids.

Non-ionic surfactants are preferably polyglycol ether derivatives of aliphatic or cycloaliphatic alcohols, or saturated or unsaturated fatty acids and alkylphenols, said derivatives containing 3 to 30 glycol ether groups and 8 to 20 carbon atoms in the (aliphatic) hydrocarbon moiety and 6 to 18 carbon atoms in the alkyl moiety of the alkylphenols.

Further suitable non-ionic surfactants are the water-soluble adducts of polyethylene oxide with polypropylene glycol, ethylenediamino-propylene glycol and alkylpolypropylene glycol containing 1 to 10 carbon atoms in the alkyl chain, which adducts contain 20 to 250 ethylene glycol ether groups and 10 to 100 propylene glycol ether groups. These compounds usually contain 1 to 5 ethylene glycol units per propylene glycol unit.

Representative examples of non-ionic surfactants are nonylphenolpolyethoxyethanols, castor oil polyglycol ethers, polypropylene/polyethylene oxide adducts, tributylphenoxypolyethoxyethanol, polyethylene glycol and octylphenoxypolyethoxyethanol. Fatty acid esters of polyoxyethylene sorbitan, e.g. polyoxyethylene sorbitan trioleate, are also suitable non-ionic surfactants.

Cationic surfactants are preferably quaternary ammonium salts which contain, as N-substituent, at least one $C_8$–$C_{22}$alkyl radical and, as further substituents, unsubstituted or halogenated lower alkyl, benzyl or hydroxy-lower alkyl radicals. The salts are preferably in the form of halides, methylsulfates or ethylsulfates, e.g. stearyltrimethylammonium chloride or benzyl di(2-chloroethyl)ethylammonium bromide.

The surfactants customarily employed in the art of formulation are described e.g. in the following publications:

"1987 International McCutcheon's Detergents and Emulsifiers", Glen Rock, N.J., USA; Dr. Helmut Stache, "Tensid Taschenbuch" (Handbook of Surfactants), 2nd edition, Carl Hanser Verlag, Munich/Vienna 1981.

The formulations of this invention usually contain 0.1 to 95%, preferably 0.1 to 80%, of a mixture of active components, 1 to 99.9%, of a solid or liquid adjuvant, and/or 0 to 25%, preferably 0.1 to 25%, of a surfactant.

Preferred formulations are composed in particular of the following constituents (%=percentage by weight):

| Emulsifiable concentrates | |
|---|---|
| compound of formula I: | 1 to 20%, preferably 5 to 10% |
| surfactant: | 5 to 30%, preferably 10 to 20% |
| liquid carrier: | 50 to 94%, preferably 70 to 85% |
| Dusts | |
| compound of formula I: | 0.1 to 10%, preferably 0.1 to 1% |
| solid carrier: | 99.9 to 90%, preferably 99.9 to 99% |
| Suspension concentrates | |
| compound of formula I: | 5 to 75%, preferably 10 to 50% |
| water: | 94 to 25%, preferably 88 to 30% |
| surfactant: | 1 to 40% preferably 2 to 30% |
| Wettable powders | |
| compound of formula I: | 0.5 to 90%, preferably 1 to 80% |
| surfactant: | 0.5 to 20%, preferably 1 to 15% |
| solid carrier: | 5 to 95%, preferably 15 to 90% |
| Granulates | |
| compound of formula I: | 0.5 to 30%, preferably 3 to 15% |
| solid carrier: | 99.5 to 70%, preferably 99 to 85%. |

Whereas commercial products will be preferably formulated as concentrates, the end user will normally employ dilute formulations. The formulations can be diluted to a concentration as low as 0.001% of active substance. The rates of application are usually from 0.001 to 4 kg a.s./ha, preferably from 0.005 to 1 kg a.s./ha.

The compositions may also contain further ingredients such as stabilisers, antifoams, viscosity regulators, binders, tackifiers, as well as fertilisers and other compounds for obtaining special effects.

The following Examples illustrate the invention.

Preparation examples

P.1.

1-(4-chloro-2-fluoro-5-isopropoxyphenyl)-4-cyclopropyl-piperidine-2,6-dione

P.1.1. N-(4-chloro-2-fluoro-5-isopropoxyphenyl)-3-cyclopropylglutaric acid-monoamide 8.7 g (0.043 mole) of 4-chloro-2-fluoro-5-isopropoxyaniline and 6.6 g (0.043 mole) of 3-cyclopropylglutaric acid-anhydride are suspended in 120 ml of benzene while the suspension is heated. The reaction mixture is stored over night at room temperature and then condensed at the rotatory evaporator. The residue is recrystallized from diisopropyl ether. Thus 13.1 g of the title product of the formula

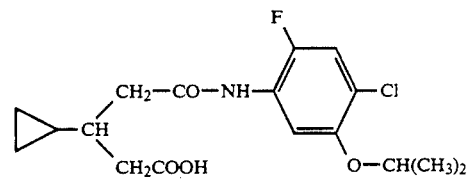

are isolated with a melting point of 110°–112° C.

P.1.2.

1-(4-chloro-2-fluoro-5-isopropoxyphenyl)-4-cyclopropyl-piperidine-2,4-dione 10.0 g (0.028 mole) of the glutaric acid-monoanilide, obtained according to example P.1.1., and 2.3 g (0.028 mole) of sodium acetate are suspended in 110 ml of acetic acid anhydride and stirred for 30 minutes at a temperature of 80° C. Unreacted acetic acid anhydride and developed acetic acid are distilled under vacuum. The residue is mixed with water and acetic acid ethyl ester, the organic phase is washed subsequently with ice-water, a 10% sodium bicarbonate solution, ice-water and saturated sodium chloride solution and then dried over sodium sulfate. The mixture is then condensed at the rotatory evaporator. The remaining residue is recrystallized from diisopropyl ether. This one isolated 8.1 g of the title product of the formula

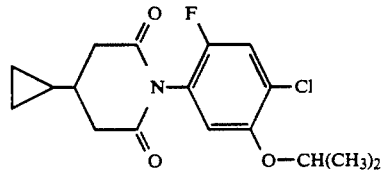

as crystals with a melting point of 130°–132° C. (compound No. 4.01).

Preparation of intermediate products
3-cyclopropyl-glutaric acid-anhydride 3-cyclopropyl-glutaric acid-anhydride can be prepared according to the following scheme:

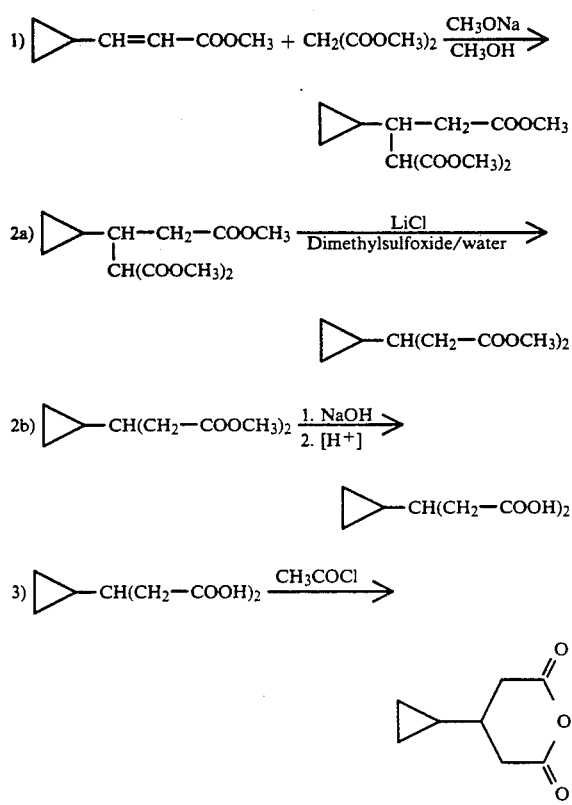

P.2.1. 2-cyclopropyl-propane-1,1,3-tricarbonic acid-trimethyl-ester 42.4 g (0.336 mole) 3-cyclopropyl-acrylic-acid-methyl-ester, 58.9 ml (0.504 mole) malonic-acid-dimethyl-ester and 12.4 ml (0.067 mole) 5.4 molar methanolic sodium methylate are dissolved in 135 ml of methanol and heated under reflux for 5 hours. The reaction mixture is cooled to room temperature and then condensed at the rotatory evaporator. After addition of ice water the residue is neutralized with acetic acid and then extracted with diethyl ether. The organic phase is separated and then dried over sodium sulfate. After evaporating the ether there remains an oil which is fractionated. Thus 75.4 g of the title product are obtained with a boiling point of 113° C. at $10^{-2}$ mm Hg.

P.2.2. 3-cyclopropyl-glutaric acid 91 g (0.352 mole) 2-cyclopropyl-propane-1,1,3-tricarbonic acid trimethyl ester, 14.9 g (0.352 mole) lithium chloride and 12.7 ml (0.704 mole) water are refluxed in 490 ml dimethylsulfoxide for 1 day. The reaction mixture is cooled to room temperature, poured on ice water and extracted with ethyl acetate. The combined organic phases are dried over sodium sulfate and evaporated. 52.8 g of the diester remains as a light colored liquid which is then stirred in 360 ml 2M NaOH for 2 days at room temperature. The reaction mixture is acidified with 5M sulfuric acid, saturated with sodium chloride and then extracted with ethyl acetate. The combined fractions are then dried over sodium sulfate and filtered. After evaporating the organic solvent the remaining residue is recrystallized from diisopropyl ether, and 15.6 g of the title product with a melting point of 75°–77° C. are isolated.

P.2.3. 3-cyclopropyl-glutaric acid anhydride 18.7 g (0.1086 mole) 3-cyclopropyl-glutaric acid are added to 40 ml of acetyl chloride. The reaction mixture is stirred at room temperature and then the temperature is raised to the boiling point until no HCl-development is noticeable. Then unreacted acetyl chloride is distilled under normal pressure and then the formed acetic acid is distilled under vacuum. The remaining residue is stirred with diisopropyl ether. After filtration 13.2 g of the title product is isolated with a melting point of 40°–43° C.

In analogy to the above preparation examples, the compounds of the tables 1 to 4 are obtained:

Compounds of the formula

TABLE 1

(Ig)

| | R | R₁ | R₂ | R₈ |
|---|---|---|---|---|
| 1.01 | ◁ | F | Cl | H |

Compounds of the formula

TABLE 2

(Ic)

| | R | R₁ | R₂ | R₈ | R₄ |
|---|---|---|---|---|---|
| 2.01 | ◁ | F | Cl | —CH₃ | —CH₃ |
| 2.02 | ◁ | F | Cl | —CH₃ | —CH(CH₃)—COOCH₃ |
| 2.03 | ◁ | F | Cl | —CH₃ | —CH₂—CH=CHCl |

Compounds of the formula

TABLE 3

Compounds of the formula (Ib):

$$\text{R}-\underset{O}{\overset{O}{\underset{\|}{\bigcirc}}}-N-\text{Ar}(R_1)(R_2)(COR_3)$$

| | R | $R_1$ | $R_2$ | $R_3$ |
|---|---|---|---|---|
| 3.01 | cyclopropyl | F | Cl | OH |
| 3.02 | cyclopropyl | F | Cl | $OCH_3$ |
| 3.03 | cyclopropyl | F | Cl | $OC_2H_5$ |
| 3.04 | cyclopropyl | F | Cl | $O-CH(CH_3)_2$ |
| 3.05 | cyclopropyl | F | Cl | $O-C_5H_{11}(n)$ |

Compounds of the formula

TABLE 4

Formula (Ih):

| | R | $R_1$ | $R_2$ | X | $R_4$ | |
|---|---|---|---|---|---|---|
| 4.01 | cyclopropyl | F | Cl | O | $-CH(CH_3)_2$ | m.p. 130–132° C. |
| 4.02 | cyclopropyl | F | Cl | O | $-CH_2-C\equiv CH$ | m.p. 127–128° C. |
| 4.03 | cyclopropyl | F | Cl | O | $-CH(CH_3)-C\equiv CH$ | |
| 4.04 | cyclopropyl | F | Cl | O | $-CH_3$ | |
| 4.05 | cyclopropyl | F | Cl | O | $-C_2H_5$ | |
| 4.06 | cyclopropyl | F | Cl | O | $-C_4H_9(n)$ | |
| 4.07 | cyclopropyl | F | Cl | O | $-C_4H_9(i)$ | |
| 4.08 | cyclopropyl | F | Cl | O | $-C_4H_9(s)$ | |

B. Biological Examples

Example B1: Pre-emergence herbicidal action

In a greenhouse, immediately after sowing the test plants in seed trays the surface of the soil is treated with an aqueous dispersion of the test compound obtained from a 25% emulsifiable concentrate. Various rates of application of active ingredient/hectare are tested. The seed trays are kept in the greenhouse at 22°–25° C. and 50–70% relative humidity and the test is evaluated after 3 weeks.

The herbicidal action is assessed in comparison with an untreated control group using a nine-stage evaluation scale (1=total damage of the test plants, 9=no herbicidal action on the test plants).

Ratings of 1 to 4 (especially 1 to 3) indicate a good to very good herbicidal action. Ratings of 6 to 9 (especially 7 to 9) indicate a good tolerance (especially in the case of crop plants).

In this test the compounds of tables 1 to 4 show e.g. at application rates of 125 to 500 g of active substance [AS] per hectare good herbicidal action against various weeds while being at the same time very compatible to the culture plants like barley, wheat, maize, soya, cotton and sun flowers.

Specific results are resumed in table 5.

TABLE 5

| Compound No. | 4.01 | 4.02 |
|---|---|---|
| application rate g/ha | 125 | 125 |
| barley | 8 | 7 |
| wheat | 9 | 8 |
| maize | 9 | 8 |
| soya | 9 | 9 |
| cotton | 9 | 9 |
| sun-flower | 9 | 7 |
| Abutilon | 1 | 1 |
| *Sida spinosa* | 1 | 1 |
| Amaranthus | 1 | 1 |
| Chenopodium Sp. | 2 | 2 |
| *Viola tricolor* | 1 | 1 |
| Veronica sp. | 1 | 1 |

Example B2: Post-emergence herbicidal action

A number of weeds, both monocotyledons and dicotyledons, are sprayed after emergence (at the 4- to 6-leaf stage) with an aqueous dispersion of active ingredient at a rate of 125 to 500 g of active ingredient per hectare and kept at 24°–26° C. and 45–60% relative humidity. 15 days after the treatment the test is evaluated in accordance with the evaluation scheme described above. The tested compounds of tables 1 to 4 show also in this test good to very good herbicidal activity.

Specific results are resumed in table 6.

TABLE 6

| Compound No. | 4.01 | 4.02 |
|---|---|---|
| application rate g/ha | 125 | 125 |
| sorghum | 9 | 8 |
| wheat | 8 | 7 |
| maize | 8 | 7 |
| soya | 8 | 9 |
| Abutilon | 1 | 1 |
| *Sida spinosa* | 3 | 3 |
| *Solanum nigrum* | 3 | 2 |
| *Sinapis album* | 4 | 2 |

Example B3: Herbicidal action before emergence of the plants

Plastics pots are filled with expanded vermiculite (density 0.135 g/cm³, water absorption capacity 0.565 liters/liter). After saturating the non-adsorptive vermiculite with an aqueous emulsion of active ingredient in deionised water which contains the active ingredients in a concentration of 70.8 ppm seeds of the following plants are sown on the surface: *Nasturtium officinalis*, *Agrostis tenuis*, *Stellaria media* and *Digitaria sanguinalis*. The test vessels are then kept in a climatic chamber at 20° C., an illumination of about 20 kLux and a relative humidity of 70%. During the germination phase of 4 to 6 days, the pots are covered with transparent material and watered with deionised water to increase the local humidity. After the fifth day, 0.5% of a commercially customary liquid fertiliser (®Greenzit) is added to the water used for watering 12 days after sowing, the test is evaluated. The compounds from tables 1 to 4 that were tested showed in this summary test good herbicidal action.

Formulation Examples

Example F 1: Formulation Examples for compounds of formula I (throughout, percentages are by weight)

| a) Emulsifiable concentrates | a) | b) | c) |
|---|---|---|---|
| a compound of Tables 1 to 4 | 25% | 40% | 50% |
| calcium dodecylbenzenesulfonate | 5% | 8% | 5.8% |
| castor oil polyethylene glycol ether (36 moles of ethylene oxide) | 5% | — | — |
| tributylphenol polyethylene glycol ether (30 moles of ethylene oxide) | — | 12% | 4.2% |
| cyclohexanone | — | 15% | 20% |
| xylene mixture | 70% | 25% | 20% |

Emulsions of any required concentration can be produced from such concentrates by dilution with water.

| b) Solutions | a) | b) | c) |
|---|---|---|---|
| a compound of Tables 1 to 4 | 80% | 10% | 5% |
| ethylene glycol monomethyl ether | 20% | — | — |
| polyethylene glycol (mol. wt. 400) | — | 70% | — |
| N-methyl-2-pyrrolidone | — | 20% | 5% |
| epoxidised coconut oil | — | — | 90% |

These solutions are suitable for application in the form of microdrops.

| c) Granules | a) | b) |
|---|---|---|
| a compound of Tables 1 to 4 | 5% | 10% |
| kaolin | 94% | — |
| highly dispersed silicic acid | 1% | — |
| attapulgite | — | 90% |

The active ingredient is dissolved in methylene chloride, the solution is sprayed onto the carrier, and the solvent is subsequently evaporated off in vacuo.

| d) Dusts | a) | b) | c) |
|---|---|---|---|
| a compound of Tables 1 to 4 | 2% | 5% | 8% |
| highly dispersed silicic acid | 1% | 5% | 5% |
| talcum | 97% | — | 10% |

-continued

| d) Dusts | a) | b) | c) |
|---|---|---|---|
| kaolin | — | 90% | 77% |

Ready-for-use dusts are obtained by intimately mixing the carriers with the active ingredient.

| e) Wettable powders | a) | b) |
|---|---|---|
| a compound of Tables 1 to 4 | 20% | 60% |
| sodium lignosulfonate | 5% | 5% |
| sodium lauryl sulfate | 3% | 6% |
| octylphenol polyethylene glycol ether (7-8 moles of ethylene oxide) | — | 2% |
| highly dispersed silicic acid | 5% | 27% |
| kaolin | 67% | — |

The active ingredient is thoroughly mixed with the adjuvants and the mixture is thoroughly ground in a suitable mill, affording wettable powders which can be diluted with water to give suspensions of the desired concentration.

| f) Extruder granulate | |
|---|---|
| a compound of Tables 1 to 4 | 10% |
| sodium lignosulfonate | 2% |
| carboxymethylcellulose | 1% |
| kaolin | 87% |

The active ingredient is mixed and ground with the adjuvants, and the mixture is subsequently moistened with water. The mixture is extruded and then dried in a stream of air.

| g) Coated granulate | |
|---|---|
| a compound of Tables 1 to 4 | 3% |
| polyethylene glycol (mol. wt. 200) | 3% |
| kaolin | 94% |

The finely ground active ingredient is uniformly applied, in a mixer, to the kaolin moistened with polyethylene glycol. Non-dusty coated granulates are obtained in this manner.

| h) Suspension concentrate | |
|---|---|
| a compound of Tables 1 to 4 | 40% |
| ethylene glycol | 10% |
| nonylphenol polyethylene glycol (15 moles of ethylene oxide) | 6% |
| sodium lignosulfonate | 10% |
| carboxymethylcellulose | 1% |
| 37% aqueous formaldehyde solution | 0.2% |
| silicone oil in the form of a | 75% |
| aqueous emulsion | 0.8% |
| water | 32% |

The finely ground active ingredient is intimately mixed with adjuvants, giving a suspension concentrate from which suspensions of any desired concentration can be obtained by dilution with water.

What is claimed is:

1. A 1-phenyl-piperidine-2,6-dione of the formula I

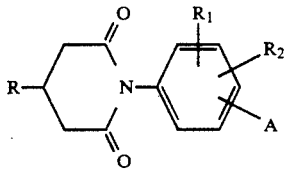 (I)

wherein
R is $C_3-C_7$-cycloalkyl;
$R_1$ is hydrogen; or halogen;
$R_2$ is hydrogen; cyano; nitro; or halogen;
A is hydrogen; cyano; nitro; $COR_3$; $XR_4$;

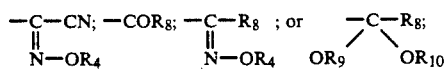

$R_3$ is halogen; $X'-R_5$; amino; $C_1-C_4$-alkylamino; di-$C_1-C_4$-alkylamino; $C_2-C_4$-halogenalkylamino; $C_1-C_4$-hydroxyalkylamino; di-$C_1-C_4$-hydroxyalkylamino; $C_3-C_4$-alkenylamino; diallylamino; N-pyrrolidino; N-piperidino; N-morpholino; N-thiomorpholino; or N-piperazino;

$R_4$ is hydrogen; $C_1-C_{10}$-alkyl; $C_1-C_4$-alkoxy-$C_1-C_4$-alkyl; $C_1-C_4$-alkylthio-$C_1-C_4$-alkyl; di-$C_1-C_4$-alkylamino-$C_1-C_4$-alkyl; halo-$C_1-C_8$-alkyl; $C_3-C_8$-alkenyl; halo-$C_2-C_8$-alkenyl; $C_3-C_8$-alkynyl; $C_3-C_7$-cycloalkyl; halo-$C_3-C_7$-cycloalkyl; $C_1-C_8$-alkylcarbonyl; allylcarbonyl; $C_3-C_7$-cycloalkylcarbonyl; benzoyl unsubstituted or substituted at the phenyl ring identically or differently up to three times by halogen, $C_1-C_4$-alkyl, halo-$C_1-C_4$-alkyl, halo-$C_1-C_4$-alkoxy, or $C_1-C_4$-alkoxy; furanoyl; thiophenoyl; $C_1-C_4$-alkyl that is substituted by phenyl, halophenyl, $C_1-C_4$-alkylphenyl, $C_1-C_4$-alkoxyphenyl, halo-$C_1-C_4$-alkylphenyl, halo-$C_1-C_4$-alkoxyphenyl, $C_1-C_6$-alkoxycarbonyl, $C_1-C_4$-alkoxy-$C_1-C_8$-alkoxycarbonyl, $C_3-C_8$-alkenyloxycarbonyl, $C_3-C_8$-alkynyloxycarbonyl, $C_1-C_6$-alkylthiocarbonyl, $C_3-C_8$-alkenylthiocarbonyl, $C_3-C_8$-alkynylthiocarbonyl, carbamoyl, mono-$C_1-C_4$-alkylaminocarbonyl, di-$C_1-C_4$-alkylaminocarbonyl, phenylaminocarbonyl, wherein the phenyl ring is unsubstituted or identically or differently substituted up to three times by halogen, $C_1-C_4$-alkyl, halogen-$C_1-C_4$-alkyl, halogen-$C_1-C_4$alkoxy, or $C_1-C_4$-alkoxy, or the phenyl is monosubstituted by cyano or nitro; dioxan-2-yl which is unsubstituted or substituted by one or two $C_1-C_4$-alkyl radicals; or $C_1-C_4$-alkyl substituted by cyano, nitro, carboxyl, $C_1-C_8$-alkylthio-$C_2-C_8$-alkoxycarbonyl or $C_1-C_8$-alkoxy-$C_2-C_8$-alkoxycarbonyl;

X is oxygen; or sulfur;
X' is oxygen; or sulfur;
$R_5$ is hydrogen; $C_1-C_{10}$-alkyl; $C_1-C_4$-alkoxy-$C_1-C_4$-alkyl; halo-$C_1-C_8$-alkyl; $C_1-C_{10}$-alkylthio-$C_1-C_4$-alkyl; di-$C_1-C_4$-alkylamino-$C_1-C_4$-alkyl; cyano-$C_1-C_{10}$-alkyl; $C_3-C_8$-alkenyl; halogen-$C_3-C_8$-alkenyl; $C_3-C_8$-alkynyl; $C_3-C_7$-cycloalkyl; $C_3-C_7$-cycloalkyl-$C_1-C_4$-alkyl; halo-$C_3-C_7$-cycloalkyl; benzyl which is unsubstituted or substituted in the phenyl ring identically or differently up to three times by halogen, $C_1-C_4$-alkyl, halo-$C_1-C_4$-alkyl, halo-$C_1-C_4$-alkoxy or $C_1-C_4$-alkoxy; an alkaline-, alkaline-earth- or an ammonium-ion; or the group —$COOR_7$;

$R_6$ is hydrogen; or $C_1-C_4$-alkyl;
$R_7$ is hydrogen; $C_1-C_6$-alkyl; $C_3-C_8$-alkenyl; $C_3-C_8$-alkynyl; $C_1-C_8$-alkoxy-$C_2-C_8$-alkyl; $C_1-C_8$-alkylthio-$C_2-C_8$-alkyl; or $C_3-C_7$-cycloalkyl;
$R_8$ hydrogen; $C_1-C_4$-alkyl; halogen-$C_1-C_4$-alkyl; or $C_1-C_4$-alkoxy-$C_1-C_4$-alkyl;
$R_9$ and $R_{10}$ independently of each other are $C_1-C_4$-alkyl; $C_2-C_4$-haloalkyl; or $C_2-C_8$-alkoxyalkyl; or
$R_9$ and $R_{10}$ together from an ethylene- or propylene-bridge or a 1,2-Cyclohexanyl-ring, which radicals can be unsubstituted or substituted by one or two substitutents selected from among halogen, $C_1-C_4$-alkyl, $C_1-C_4$-haloalkyl or $C_1-C_4$-hydroxyalkyl;
$R_{11}$ is hydrogen; $C_1-C_5$-alkyl; or $C_3-C_7$-alkenyl;
$R_{12}$ is independently of each other hydrogen; or $C_1-C_8$-alkyl;
n is zero;, 1; 2; 3; or 4;
or a salt which a compound of formula I can form with an acid or a base, or a stereoisomeric form of a compound of the formula I.

2. A 1-phenyl-piperidine-2,6-dione according to claim 1, wherein R is cyclopropyl.

3. A 1-phenyl-piperidine-2,6-dione according to claim 1, of the formula Ib

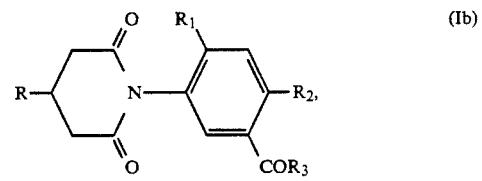 (Ib)

wherein R, $R_1$, $R_2$ and $R_3$ have the meanings given in claim 1.

4. A 1-phenyl-piperidine-2,6-dione according to claim 1, of the formula Ic

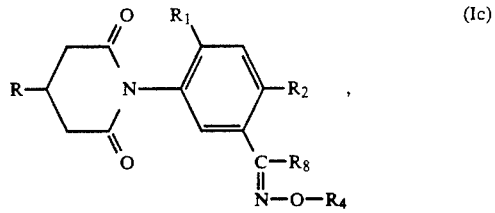 (Ic)

wherein R, $R_1$, $R_2$, $R_4$ and $R_8$ have the meanings given in claim 1.

5. A 1-phenyl-piperidine-2,6-dione according to claim 1, of the formula Ig

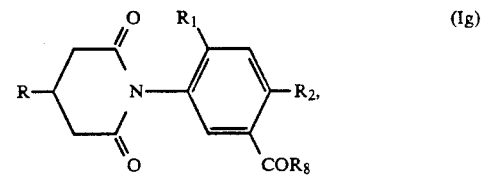 (Ig)

wherein R, $R_1$, $R_2$, and $R_8$ have the meanings given in claim 1.

6. A 1-phenyl-piperidine-2,6-dione according to claim 1, of the formula Ih

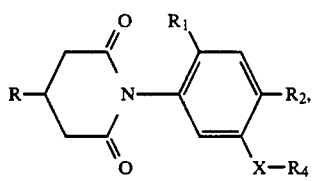

wherein R, $R_1$, $R_2$, $R_4$, and X have the meanings given in claim 1.

7. A 1-phenyl-piperidine-2,6-dione according to claim 1, of the formula Ik

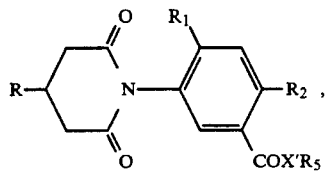

wherein R, $R_1$, $R_2$, $R_5$ and X' have the meanings given in claim 1.

8. A 1-phenyl-piperidine-2,6-dione according to claim 1, wherein $R_1$ is fluorine, $R_2$ is chlorine and the radicals A and R are as defined in claim 1.

9. A 1-phenyl-piperidine-2,6-dione according to claim 1, wherein
  R is cyclopropyl;
  $R_1$ is fluorine;
  $R_2$ is chlorine; and
  A is —COOH, —COO—$C_1$-$C_{10}$-alkyl, —O—$C_1$-$C_{10}$-alkyl, propin-3-yl, 3-methylpropin-3-yl or

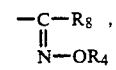

wherein $R_8$ is methyl and $R_4$ is $C_1$-$C_{10}$alkyl, halo-$C_2$-$C_8$-alkenyl or $C_1$-$C_6$-alkoxycarbonyl-$C_1$-$C_4$-alkyl.

10. A 1-phenyl-piperidine-2,6-dione according to claim 9, wherein A is —COOH, —COOCH$_3$, —COOC$_2$H$_5$, —COO(n)C$_3$H$_7$, —COO(n)C$_5$H$_{11}$, —O—CH$_3$, —O—C$_2$H$_5$, —O—(i)C$_3$H$_7$, —O—(n)C$_4$H$_9$, —O—(i)C$_4$H$_9$, —O—(sek)C$_4$H$_9$, propin-3-yl, 3-methylpropin-3-yl or

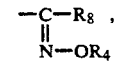

wherein $R_8$ is methyl and $R_4$ is methyl, 1-chloropropen-3-yl or —CH(CH$_3$)—COOCH$_3$.

11. A herbicidal composition which contains besides inert carrier material and additives and a wetting agent as active ingredient a herbicidally active amount of a 1-phenyl-piperidine-2,6-dione according to claim 1.

12. A method for controlling undesirable plant-growth which comprises applying to the plants to be controlled or their locus, a herbicidally effective amount of a compound according to claim 1 or of a composition containing such a compound.

13. A method according to claim 12 for controlling weeds in cultures of sorghum, rice, cotton, soybeans and sun-flowers.

* * * * *